(12) United States Patent
Dorn (10) Patent No.: US 9,953,136 B2
(45) Date of Patent: Apr. 24, 2018

(54) SYSTEM FOR DISPLAYING AND EDITING DATA FOR A MEDICAL DEVICE

(71) Applicant: SIEMENS HEALTHCARE GMBH, Erlangen (DE)

(72) Inventor: Karlheinz Dorn, Kalchreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/116,024

(22) PCT Filed: Feb. 20, 2014

(86) PCT No.: PCT/EP2014/053356
§ 371 (c)(1),
(2) Date: Aug. 2, 2016

(87) PCT Pub. No.: WO2015/124192
PCT Pub. Date: Aug. 27, 2015

(65) Prior Publication Data
US 2017/0177794 A1 Jun. 22, 2017

(51) Int. Cl.
*G06T 15/08* (2011.01)
*G06T 19/00* (2011.01)
*G06T 1/60* (2006.01)
*G06T 11/60* (2006.01)
*G06F 19/00* (2018.01)

(52) U.S. Cl.
CPC .............. *G06F 19/321* (2013.01); *G06T 1/60* (2013.01); *G06T 11/60* (2013.01); *G06T 15/08* (2013.01); *G06T 2200/24* (2013.01); *G06T 2210/41* (2013.01)

(58) Field of Classification Search
CPC .................................................... G06F 19/321
See application file for complete search history.

(56) References Cited

U.S. PATENT DOCUMENTS

| | | | |
|---|---|---|---|
| 7,702,719 B1 | 4/2010 | Betz et al. | |
| 2005/0228250 A1* | 10/2005 | Bitter | A61B 5/02007 600/407 |
| 2009/0074280 A1* | 3/2009 | Lu | A61B 8/00 382/131 |
| 2010/0049740 A1 | 2/2010 | Iwase et al. | |
| 2012/0185874 A1 | 7/2012 | Cookson | |

(Continued)

OTHER PUBLICATIONS

Tupec, Pavel. "Software for planning of operations and tool evidence for medical facilities." Charles University in Prague, Department of Software Engineering, Thesis 2010.*

(Continued)

*Primary Examiner* — Daniel Hajnik
(74) *Attorney, Agent, or Firm* — Lempia Summerfield Katz LLC (57) ABSTRACT

A system for displaying and editing data for a medical device is provided. The system includes at least one viewing application for execution on a user appliance, which application is set up to display medical image data records that are kept in cloud storage in a public cloud. In respect of its component architecture, the viewing application includes a View layer, a ViewModel layer, a Model layer, and a driver layer. In this case, the ViewModel layer defines a common set of functions for the display and editing of 2D image data and 3D image data.

11 Claims, 5 Drawing Sheets

(56) References Cited

U.S. PATENT DOCUMENTS

2013/0185318 A1\*  7/2013  Hirai ................... G06F 17/3089
                                                              707/756
2013/0208966 A1    8/2013  Zhao et al.
2013/0290404 A1   10/2013  Rajabi et al.
2013/0308839 A1\* 11/2013  Taylor ................... G06F 19/321
                                                              382/128
2014/0275807 A1\*  9/2014  Redei ..................... G06Q 50/24
                                                              600/300

OTHER PUBLICATIONS

Márquez, Carlos Luis Castro, and Alejandro Delgado García. "SLD060 Visor De Imágenes Médicas Digitales Web." "IX Congreso Internacional Informática en Salud 2013", Mar. 2013, along with corresponding English translation.\*

Bahga et al; "A cloud-based approach for interoperable electronic Health records (EHRs)", IEEE Journal of Biomedical and health informatics, IEEE; bd. 17; nr. 5; pp. 894-906, ISSN: 2168-2194, DOI: 10.1109/JBHI.2013.2257818, XP011525485, 2013.

Patel et al; DICOM Medical Image Management the challenges and solutions: Cloud as a Service (CaaS); Computing Communication & Networking Technologies (ICCNT), third international conference on IEEE, pp. 1-5, DOI: 10.1109/ICCNT.2012.6396083, XP032443043, 2012.

\* cited by examiner

SYSTEM FOR DISPLAYING AND EDITING DATA FOR A MEDICAL DEVICE

The present patent document is a § 371 nationalization of PCT Application Serial Number PCT/EP2014/053356, filed Feb. 20, 2014, designating the United States, which is hereby incorporated by reference.

TECHNICAL FIELD

The embodiments relate to a system for management and processing of data of a medical facility.

BACKGROUND

The term "management" refers to the archiving of the data (meaning the storage of the data in persistent memory), the reproduction (display) and the deletion of the data from the data memory, as well as the sorting and finding of particular data from the data memory in accordance with predetermined criteria (browsing).

The term "processing" may refer to the modification (editing/preparation) of the data.

The data of the medical facility to be managed and processed includes patient data, works/tasks or worklists for the personnel of the medical facility and medical image data.

The management of such medical data is increasingly undertaken with the support of computers by server systems, e.g., so-called information systems. An information system includes: (1) one or more data memories, e.g., in the form of a storage area network (SAN); (2) one or more associated data servers; (3) at least one relational database that is implemented in a database server; (4) one or more further servers, for example, in which methods for database access and data processing are implemented.

Different medical information systems have established themselves in the medical field for the different types of data. Thus, in the environment of a medical facility, such as a clinic for example, a Hospital Information System (HIS) is used for the management and processing of patient data, and a Radiology Information System (RIS) is used for scheduling radiological examinations, supporting the diagnosis of medical imaging data and documentation of the diagnoses. In addition, the IT structure of a hospital may include a so-called Picture Archiving and Communication System (PACS) for archiving and communicating medical image data on the basis of the DICOM standard as well as an Advanced Visualization (AV) system that provides server-supported functions for visualizing volume data, e.g., dynamic volume rendering.

The aforementioned server systems, in this case, are as a rule present in parallel to one another. This demands a high outlay in procurement and maintenance, which is barely affordable, in particular for small medical facilities or any other facility with a comparatively low finance volume.

The complex IT structure of a modern medical facility described above also has only comparatively poor scaling properties. Adapting such an IT structure to greater changes in the volume of data to be processed and archived and/or to the required computing power is thus mostly only possible with a comparatively high outlay.

Personal computers (PCs) have previously predominantly been used as users or terminals (classically referred to as clients) of such an IT structure, wherein these PCs are often embodied as so-called thin clients that obtain a majority of their required processing power from a connected server. In recent times, however, there has been an increasing desire also to use mobile small computers such as smartphones, tablets, or PDAs as the user device.

A further problem of conventional information systems in the medical environment lies in the fact that the front-end software of these systems may be specifically and rigidly oriented to the management and processing of specific data types. This leads to the front end having to be programmed and maintained separately for each information system. This, in its turn, may render the integration of innovative user devices such as smartphones and tablets into the clinical workflow more difficult, since the diversification of the software components connected with the corresponding adaptation of the respective front end is only able to be managed at great expense in respect of its production and further development. This may relate to software for display (e.g., referred to as viewing) of image data, since corresponding applications have to be provided for different image data types and also for different purposes, e.g., preliminary examination of the image data at the modality producing the image (examination), the actual diagnosis (reading) and, if necessary, just browsing.

In recent years, so-called cloud solutions have become established as an alternative to conventional client-server architectures. In such cases, a cloud is understood to be a data processing facility, which on the one hand is provided and operated by a cloud vendor independent of the user. The cloud vendor provides a plurality of users with the hardware and, if necessary, the software of the cloud as a service within the framework of a usage agreement (e.g., subscription). Depending on the scope of the services provided, a distinction is made between the following: (1) A usage pattern referred to as an "Infrastructure as a Service" (IaaS) in which the user is merely provided with computer hardware (computers, networks and memory) of the cloud, while the users themselves are fully responsible for the software operated in the cloud; (2) A usage pattern described as a "Platform as a Service" (PaaS) in which the user is offered from the cloud the computer hardware together with a programming and runtime environment building thereon, so that users themselves are only responsible for the application software (applications) implemented in this programming and runtime environment; and (3) A usage pattern designated as "Software as a Service" (SaaS), in which specific application software is also made available to the user from the cloud.

Depending on the group of users to which the respective cloud is addressed, a further distinction is made between the following: (1) What is referred to as public cloud, of which the services may be made use of by anyone; and (2) What is referred to as a private cloud, which is only accessible to users of a specific organization, e.g., of a specific company.

For each user of a public cloud, the access permissions are regulated to specific hardware and software components of the cloud by the subscription assigned to the user. This means that public clouds are regularly multi-tenant. This identifies the capability of keeping data, user management, and computing operations strictly separated for users with different subscriptions. A user of the public cloud may thus not view the data, user management, and computing operations of another user with a different subscription and also cannot influence this data.

However, the problems described above are not solved by merely transferring the classically conventional server systems into the cloud, since the complexity of the IT structure is not simplified by this, but instead is even increased. On the other hand, new problems arise because of this. In particular, the relocation of the IT structure into the cloud may result in perceptible increases of the latency times for responding to user queries. This may be tedious in viewing applications for displaying medical image data, since, conditional on latency times, the construction of the images to be viewed may perceptibly lag behind the working tempo of a user, which may lead to a marked adverse effect on the work sequences in the medical environment.

SUMMARY AND DESCRIPTION

The scope of the present invention is defined solely by the appended claims and is not affected to any degree by the statements within this summary. The present embodiments may obviate one or more of the drawbacks or limitations in the related art.

The underlying object of is to specify a system for management and processing of data of a medical facility that is able to be used, e.g., flexibly.

The system may serve to display and process medical image datasets of one of more of the following image data types: (1) 2D image data, e.g., two-dimensional, static individual medical images (such as, e.g., x-ray and ultrasound images, so-called key images, photos, and documents), but also 2D image sequences or videos; (2) 3D image data (also referred to as volume data) such as computer tomograms and MR tomograms for example; and/or (3) Chronological volume data sequences (e.g., 4D image data).

A snapshot, e.g., a (processed or unprocessed) segment from a medical image or volume dataset, which was derived during the reading of this data for representing a medical diagnosis, is referred to here as a "key image". Such key images may be used as an element of a medical report.

"Photos"—to differentiate them from the previously mentioned individual medical images and the key images—refer to an image having only indirect relevance in the medical context, e.g., portraits of patients or medical personnel, images of medical facilities, photographic copies of texts, etc.

"Documents" refer to files with image and/or text content that are not present in an original image data format but in a document format (e.g., PDF).

A 2D image sequence includes a number of two-dimensional individual images. These individual images may—in a similar way to a video—reflect the change of image information over time. Individual images, which are not in a direct chronological relationship, may be collected into an image sequence, e.g., different projections of an area of a patient's body.

The image data given above is to be distinguished in this case from other medical data, which is optionally likewise managed and processed by the system, such as (1) Patient data that includes personal and medical information about a specific patient of the facility, e.g., details of name, address, age, gender, earlier diagnoses, and treatments; (2) Works/tasks and worklists that are to be carried out by one or more medical users (doctors, medical assistants, care workers etc.) of the medical facility; and also (3) Context data, meaning context information for medical imaging data, e.g., references to the storage location of image datasets as well as optional metadata for image datasets, such as e.g., the imaging parameters underlying the respective image recording.

The datasets of a particular data type are also referred to below as "resources".

To display image data of at least one specific image data type the system has at least one viewing application for execution on a user device.

The viewing application is divided up in respect of its component architecture into at least four layers. These layers include a View layer, a ViewModel layer, a Model layer and a driver layer.

The View layer includes a number of components (e.g., at least one component, but optionally also a number of components) that are configured to define the graphic content of a GUI page to display 2D image data or to define 3D image data. In an embodiment, the View layer in this case includes two components (designated "ReadingView2D" and "ReadingView3D," for example) of which the first defines a GUI exclusively configured for presenting 2D image data (including key images, photos, 2D image sequences and videos), while the second defines a GUI exclusively configured for presenting 3D image data. The last-mentioned component may not belong to the basic equipment of the viewing application, but is optionally able to be loaded or activated at the request of the user or within the framework of a license agreement.

The component or each component of the View layer here may define the type, the appearance, and arrangement of the graphical elements of the associated GUI page, e.g., the control elements via which the information may be output to a user or user inputs and commands may be received. On the other hand, the logic connected to the control elements (UI logic) is not defined by the components of the View layer, since this function is reserved for the ViewModel layer. A GUI page here is referred to as self-contained and inherently functionally-capable part of a graphical user interface (GUI), which—somewhat like a type of window—may be operated on its own or in conjunction with further GUI pages.

The ViewModel layer includes a (e.g., just a single) component, which is referred to for example as a ReadingViewModel. As indicated above, the component of the ViewModel layer implements the UI logic, e.g., the characteristics and commands for the control elements of the GUI page defined in the component or in each component of the View layer. The ReadingViewModel may operate asynchronously and in parallel and represents a mediator between the View layer and the driver layer.

The Model layer includes a (e.g., just a single) component, which is referred to for example as a "<Tweet>ReadingModel". This component defines variables for the image data to be displayed here. It thus holds the image data to be displayed during operation of the application.

The driver layer includes at least one driver component (referred to below as "ReadingService2D"), which is configured to load 2D image data records from an image memory and edit them for display on a screen. In the case of 2D image data, the editing includes the rotation, the moving, and the enlargement/reduction of the image information. In the case of image data of which the image information is divided up into a plurality of image tiles, the editing includes the selection of the correct image tile.

The driver layer further includes a driver component (referred to below as "ReadingServiceAgent3D"), which is configured to load 3D image datasets or two-dimensional views derived herefrom from an image data memory and—where required—to edit them for display on a screen.

The View layer, the ViewModel layer and the Model layer here correspond to the basic principle in accordance with the so-called MVVM (Model View ViewModel) scheme, as may be used in the programming of applications with a graphical user interface. A significant difference between the component architecture in accordance with the application and the MVVM scheme lies in the fact that the component of the ViewModel layer (the "ReadingViewModel") is generic in the sense that it is independent of the specific image data type of the processed datasets. "Independent" means that one and the same component "ReadingViewModel" may be employed both for display and processing of 2D image data and also for display and processing of 3D image data.

The generic design of the component "ReadingViewModel" may be expressed in this case in the fact that it defines both for 2D image data (and here both for individual images and also for key images, photos, 2D image sequences, videos etc.) and also for 3D image data, in each case an identical set of functions for the control elements of the GUI page there. In particular, a same set of functions, (e.g., "Play", "Stop", "+" (zoom in), "−" (zoom out), etc.), is defined for buttons of the respective GUI page in each case by the component "ReadingViewModel" for both possibly provided components "ReadingView2D" and "ReadingView3D", wherein each of these functions is occupied by similar (e.g., always quasi-identical) semantics for different types of image data within the framework of the component "ReadingViewModel".

For example, the function "Play", in 2D image sequences, lets the individual images appear in chronological order one after the other in the manner of a slide show function. Accordingly, with video data, this function plays the videos. With 3D image data, the "Play" function causes a rotation of the 3D image information.

The "Key" function, on the other hand, triggers the creation of a key image that may be transformed into JPEG and stored, wherein for its part the type of the underlying dataset has no influence. The key image is thus created from the image data just created, regardless of whether the underlying image dataset is a 2D image dataset, a photo, a (playing or stopped) video, a (stopped or rotating) 3D image dataset, etc.

The component "<Tweet>ReadingModel" of the model layer is also designed generically in the sense that it may be reused for all image data types.

The generic design of the components of the ViewModel layer and, where necessary, the Model layer here makes possible a significant reduction in the effort of producing the viewing application or each viewing application. In particular, an almost automatic generation of the viewing application is made possible by this.

In addition, the conventional MVVM model is expanded in accordance with the teaching by at least one further layer, namely the driver layer. Through the driver layer extended right at the bottom of the layer architecture with its different driver components for 2D image data and 3D image data, a flexible (e.g., well configured to both data types and thus, in some cases, efficient) operation of the viewing application is made possible.

The component architecture of the viewing application may additionally include at least one further layer, which is designated as the "Frame layer" and is superordinate to the View layer. The frame layer includes a (e.g., just a single) component. The component of the frame layer (referred to below as the "ReadingHostAdapter") represents a generic run framework for the GUI pages defined by the components of the View layer. To the outside, the frame layer either presents itself as a native application, which is capable of being run independently on the operating system of the user device, e.g., as an IOS app, Phone-Gap-Exe, or Windows8 App. As an alternative, however, it may also be configured to run in a Web browser, and be designed in this variant as an HTML program for example. The frame layer thus serves as a software technology adapter between the or between each GUI page and the native runtime environment of the application, e.g., the operating system of the user device or a Web browser.

From the user standpoint, the frame layer here may either be invisible or itself form a superordinate part of the graphical user interface of the viewing application, and in this case may frame the displayed GUI page—in the literal sense.

Through the frame layer added at the very top of the layer architecture, it is made possible here to re-use a large part of the components of the viewing application unchanged while adapting the application to different user devices (PC, smartphone, tablet, etc.), through which the production outlay for the diversified application variants is significantly reduced.

In operation of the viewing application, the components of the superordinate layers, e.g., the components of the ViewModel layer, regularly direct queries to the driver components assigned to them in each case, e.g., the "ReadingService2D" or the "ReadinServiceAgent3D". Each of these queries is directed to the communication of image information (frame) derived from an image dataset and edited for display and is regularly triggered by an operator event (e.g., mouse event or touch event). In an advantageous version, the driver component or each driver component in this case is configured such that it processes these queries asynchronously and in parallel. However, the driver component does not present this complex processing logic to the outside. Instead, on receiving a query, it expediently does not return a direct response to the querying component, but only responds after returning the frame created because of the query. In this way, a pipeline for streaming the image information is formed, in which the data flow is not interrupted at any point by actively waiting for an answer from another component. Thus, an efficient data flow and consequently a good real time performance may be achieved.

The driver component for loading 2D image data may be configured to load image datasets directly from a predetermined data memory without a server acting as an agent. This data memory, (e.g., in an offline operating mode of the viewing application), may involve the local memory of the user device. In certain operations (e.g., online operation) of the viewing application, however, the "ReadingService2D" accesses the cloud storage of a public cloud. Here, the "ReadingService2D" may make use of neither cloud compute services nor other server power, but addresses the cloud storage directly (e.g., by an HTML, request), through which both an efficient data flow is achieved and also savings are made in operating costs to a considerable extent.

The driver component "ReadingServiceAgent3D" for loading 3D image data on the other hand may be configured, in normal operation (e.g., online mode) to have the frames to be displayed—which here, as previously mentioned, involve two-dimensional views of the three-dimensional image information, e.g., rendered image scenes—generated by (application-external) cloud compute services. In this case, the 3D image data is not itself loaded by the viewing application. Instead, the 3D image information is loaded by the cloud compute services made use of by the "ReadingServiceAgent3D". The "ReadingServiceAgent3D" only obtains the finished frames from the cloud compute services.

The "ReadingServiceAgent3D" may be able to be switched reversibly from the online mode into an offline mode, in which the "ReadingServiceAgent3D" loads the 3D image data record to be displayed into the local memory of the device and derives from the three-dimensional image information the frames for display on the screen of the device itself or by calling an application-internal service component on the user device and without making use of cloud compute services.

The image datasets may be held as part of the system in cloud storage of a public cloud such that, if a corresponding cloud subscription is available, there may be access via an associated URL directly, e.g., without making use of cloud compute services or other server power. To display one of the image datasets stored in cloud storage, the viewing application here is able to be called by specifying the URL of this image dataset as the argument, so that the viewing application, once started, loads and displays the image dataset (or in the case of 3D image data, if necessary, the frame derived therefrom) without further user action.

The viewing application itself may likewise be held in cloud storage of a public cloud, so that the viewing application, if a corresponding cloud subscription is available, may be downloaded via an associated URL. In this case, the viewing application is designed such that, in the download request, in addition to the URL of the viewing application, the URL of the image dataset to be displayed may be specified as the argument. This likewise has the consequence that the viewing application, once started, loads and displays the image dataset (or in the case of 3D image data, if necessary, the frame derived therefrom) without further user action.

The viewing application may be employed on the one hand—independently of the image-creating medical modalities—for reading the image data. On the other hand, however, it may be employed in direct conjunction with a modality for carrying out and accompanying an imaging examination.

BRIEF DESCRIPTION OF THE DRAWINGS

Exemplary embodiments are explained in greater detail below with reference to a drawing, in which:

FIG. 2 depicts a schematic block diagram of an example of technical software of the system, in accordance with which the system has specifically assigned hubs in each case for different types of data of the medical facility in cloud storage of the public cloud, e.g., a patient hub for patient datasets, a worklist hub for work, a context hub for context datasets and an image hub for image datasets, and wherein the system on each device for each hub contains an assigned application for access to the datasets stored in this hub, wherein in the three first-named hubs, table storage is set up in each case, in which for each dataset of the hub an assigned list entry (tweet) is contained, and wherein each application is configured to browse the table storage of the associated hub and to extract and display a feed of selected tweets, and wherein the application assigned in the image hub is configured for viewing the image datasets.

Parts and values that correspond to one another are labeled with the same reference characters in all figures.

DETAILED DESCRIPTION

Figure 1:
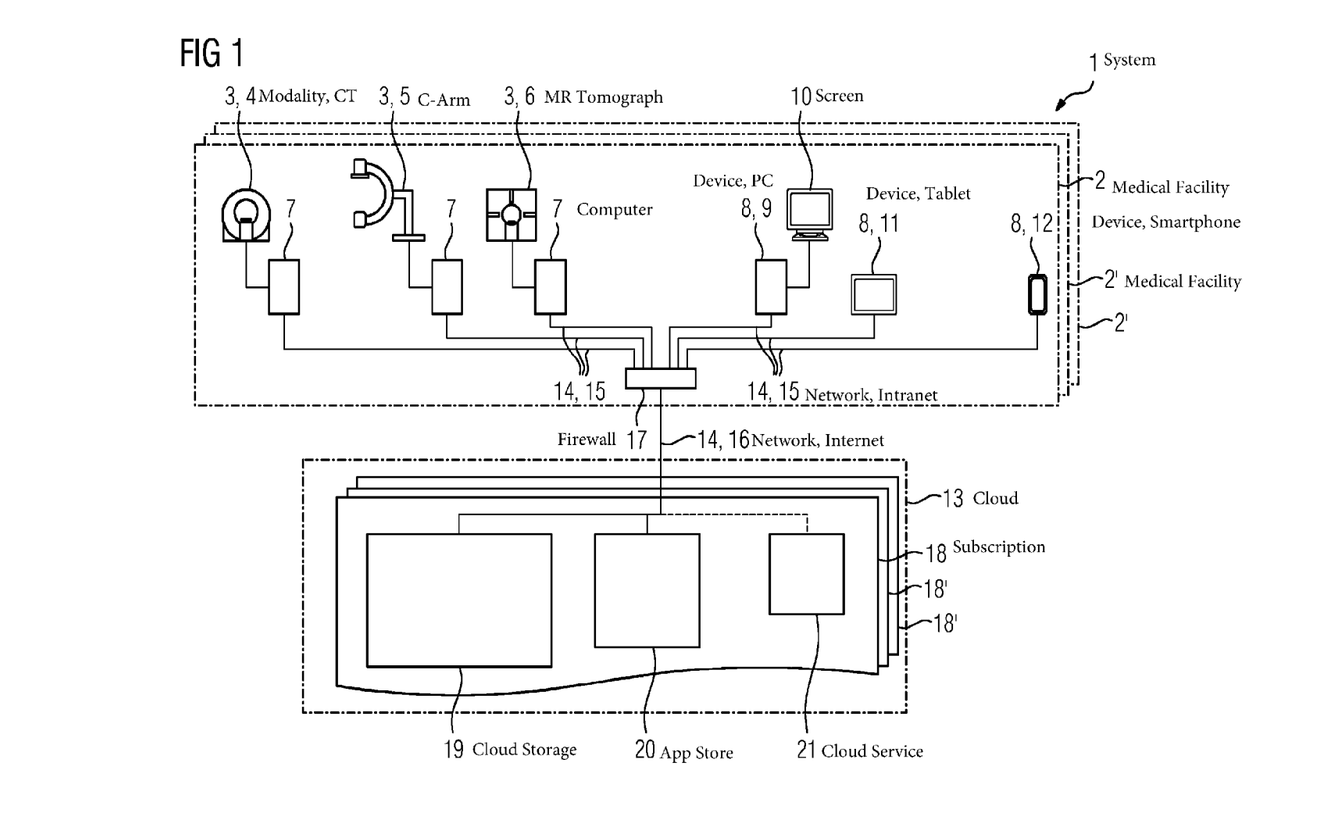
FIG. 1 depicts a schematic block diagram of an example of a system for management and processing of data of a medical facility, with a number of modalities and user devices (also referred to as terminals or devices) as well as with a public cloud connected to the modalities and devices via the Internet.

FIG. 1 depicts a rough simplified schematic diagram of a system 1 for management and processing of medical data of a medical facility 2, which involves a clinic, for example.

On the hardware side, the system 1 contains a number of modalities 3, e.g., medical imaging examination devices of the facility 2. Thus, the system 1, in the example diagram depicted in FIG. 1, includes a computed tomograph 4, a C-arm device 5 and a magnetic resonance tomograph 6. Each modality 3 is assigned a (e.g., control and evaluation) computer 7.

Furthermore, on the hardware side, the system 1 includes a number of user devices or terminals (called devices 8 below) of the facility 2 that serve to display and process data. In the simplified example in accordance with FIG. 1, the devices 8 include a personal computer 9 with connected screen 10, a tablet 11 and also a smartphone 12.

As an element disposed outside the facility 2, the system 1 includes a public cloud 13. The service offered by Microsoft under the name "Windows Azure" is used as the public cloud, for example. As an alternative, another public cloud or a combination of a number of public clouds (e.g., if necessary also from different providers) may be employed as public cloud 13.

The public cloud 13 is connected via a (e.g., data transmission) network 14 to the internal components of the system 1 within the facility, e.g., the modalities 3 and devices 8. This network connection is formed within the facility 2 by an intranet 15 of the facility 2, which is constructed for example as a Local Area Network (LAN) on the basis of wired Ethernet technology and/or as a wireless local area network (WLAN). Outside the facility 2, the network 14 is formed by the Internet 16. A firewall 17 may be disposed at the interface between the intranet 15 and the Internet 16.

The services provided by the public cloud 13 as part of the system 1 are defined by a usage agreement designated as a subscription 18. The subscription 18 in this case regulates which hardware and software elements of the public cloud 13 are accessible to the components of the system 1 within the facility. The term subscription 18 therefore refers below to that part of the public cloud 13 that is exclusively assigned to the facility 2 within the framework of the system 1. Other areas of the public cloud 13 may be allocated—as indicated in FIG. 1—to further medical facilities 2' within the framework of further subscriptions 18'. Each facility 2, 2' has exclusive access here to the data and services allocated to it in accordance with its subscription 18, 18', but not to the data and services of other facilities 2 or 2'. The public cloud 13 in this sense is multi-tenant.

In accordance with the subscription 18, the system 1 of the facility 2 is provided within the public cloud with a data memory referred to below as cloud storage 19, a memory for applications (e.g., application software) referred to below as an App Store 20 and also cloud compute services 21.

The cloud storage 19 serves as persistent storage of the data of the facility 2. The App Store 20 makes available applications, drivers and other peripheral software such as configuration files and templates for example, which may be downloaded by the internal components of the system 1 within the facility, e.g., the modalities 3 and the devices 8 and run during operation of the system 1 on the modalities (e.g., the assigned computers 7) or on the devices 8. The cloud compute services 21 are included within the framework of the system merely optionally for all computing operations that are not undertaken on the modalities 3 or the devices 8 themselves. The latter relates, e.g., to the computing power-intensive editing of 3D image data (e.g., volume data) of the respective modality for the storage (e.g., pre-processing), and/or the derivation of the rendered views (e.g., scenes or scene graphs) for the two-dimensional visualization (e.g., image synthesis, volume rendering) of such volume data.

Figure 2:
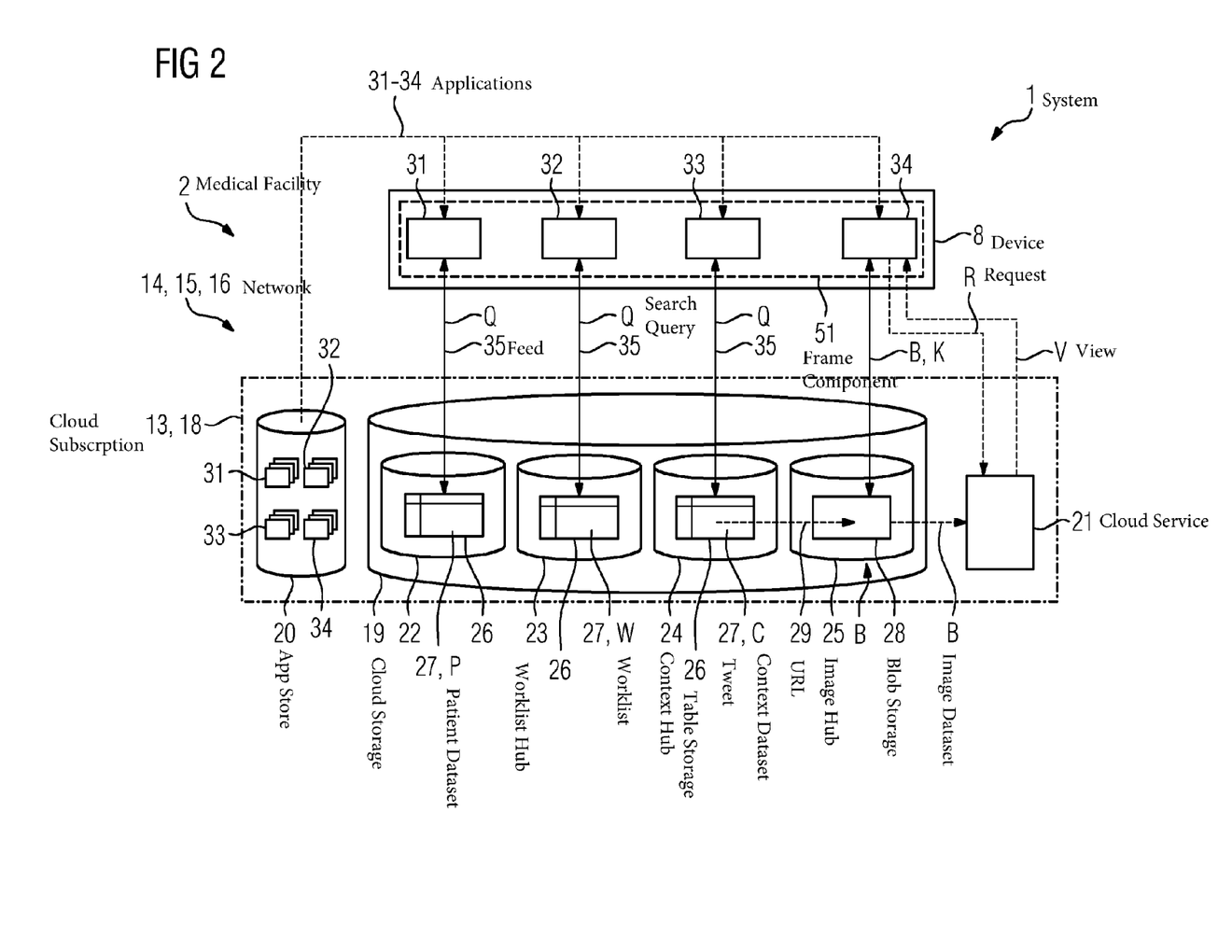

The data to be managed and processed within the framework of the facility 2 includes in accordance with FIG. 2 patient datasets P, worklists W, context datasets C and image datasets B, wherein this data individually has the content explained in greater detail above. Image datasets B here may contain medical 2D image data (e.g., including 2D image sequences, photos and videos, documents) or 3D image data (e.g., volume data) or other image, sound, graphics or text information.

In accordance with FIG. 2, for each of these different data types (e.g., resources) within the cloud storage, a separate memory area is set up in each case, which is referred to below as a (e.g., resource) hub. Thus, the following are set up individually in the cloud storage 19: a (patient) hub 22 for storing patient datasets P, a (e.g., worklist) hub 23 for storing the worklists W, a (e.g., context) hub 24 for storing the context datasets C, as well as an (image) hub 25 for storing the image datasets B.

Each of the hubs 22-24 contains a table memory (referred to below as table storage 26).

Within the framework of the system 1 a list entry, which is referred to below as a tweet 27, is set up for each stored dataset in the table storage 26 of the hub 22-24 in each case.

For datasets that, by their nature, include comparatively few discrete specifications, in such cases the entire dataset or at least a part of the same is stored as a table or list entry (e.g., tweet 27 below) in the table storage 26 of the respective hub 22-24. This relates in the example in accordance with FIG. 2 to the patient datasets P, the worklists W, as well as the context datasets C. Instead of the table storage 26 the worklist hub 23, for storing the worklists W in accordance with a first-in-first-out principle, may however also have so-called queue storage.

To store the image datasets B, which as a rule are formed from a larger and non-alphanumeric data block, so-called Blob storage 28 is provided in the image hub 25 instead of or in addition to the table storage 26, in which the image datasets are stored as "Binary Large Objects" (BLOBs) in a form that is not further structured. A context dataset C is stored as a tweet 27 in each case for the image datasets B stored in the image hub 25. This tweet contains at least one Uniform Resource Locator (URL) that identifies the storage location of the image dataset B in the Blob storage 28 of the image hub 25.

For each of the hubs 22-25, an application 31-34, which serves selectively in each case for presentation and processing of the datasets stored in the respectively assigned hub 22-25, is provided in the App Store 20. Each of the applications 31-34 thus represents the assigned hub 22-25 on the level of the device 8. The applications 31-34 are therefore also designated—in relation to the resource hubs—as application hubs.

Individually, the applications made available in the App Store 20 thus include: an application 31 for managing and processing the patient datasets P stored in the patient hub 22, an application 32 for managing and processing worklists W, an application 33 for managing and processing context datasets C, and also an application 34 for displaying and processing the image datasets B stored in the image hub 25.

The applications 31-34 may be downloaded from the App Store 20 onto each of the devices 8 and executed there. Where the system 1, as depicted in FIG. 1, includes different types of devices (e.g., personal computer 9, tablet computer 11 and/or smartphones 12), different versions of the applications 31-34 that are adapted for execution on the respective device 8 are provided in each case in the App Store 20. The applications 31-34 and their variants may not be held in a pre-fabricated state in the App Store 20. Instead, one application template in each case in the form of an XML file is held in the App Store 20 at least for the functionally-similar (e.g., browser) applications 31-33 and the (e.g., viewing) application 34, from which the respective application 31-34 is generated automatically on demand by one of the devices 8 by an application configurator on the basis of transferred configuration information. All applications 31-34 are conceived as rich client applications that are capable of running and capable of functioning without an upstream server and also without interaction with the public cloud 13.

For example, the applications 31-34 are made available for execution on the tablet computer 11 and the smartphone 12 in the form of an App configured to the respective device type, while the versions of the applications 31-34 made available for the personal computer 9 are designed to be run in a Web browser.

By comparison with a conventional IT structure for the management of medical data, from the user's standpoint the patient hub 22 and the assigned applications 31-34 assume the function of a conventional hospital information system (HIS). In particular, the entirety of personal data (e.g., and data relevant to data protection) is accepted into the patient hub 22, which thus simulates electronic patient records for the individual patient. The other hubs 23-25 may not contain any information that as such would be able to be assigned to a specific patient (e.g., privacy information). The worklist hub 23 and the assigned application 32 are presented to the user as corresponding to a conventional radiology information system (RIS), in that they list worklists to be performed within the facility 1. From the user standpoint, the context hub 24 and the assigned application 33 approximately assume the function of a conventional PACS, in that the necessary information for finding and processing image datasets is stored and is able to be researched there. Finally, the image hub 25 and the associated application 34 approximately assume the function of a conventional AV system.

Although the functions contained in the hubs 22-25 and the assigned applications 31-34 are linked to one another to a high degree, each of the hubs 22-25, together with the assigned application 31-34, is also able to be operated independently of the respective other hubs 22-25 and their applications 31-34. Thus, for example, there may be access to an image dataset B contained in the image hub 25 without the associated context dataset C of the context hub 24, if the application 34 assigned to the image hub 25 has the URL 29 of the image dataset B to be displayed made available to it in another way, e.g., by e-mail, SMS or Twitter. Furthermore, the patient data P may also be held outside the public cloud 13, since the patient hub 22 is not required for the function of the other hubs 23-25 and the assigned applications 32-34.

The application 31 assigned to the patient hub 22 involves a browser application that searches the table storage 26 of the patient hub 22 for tweets 27 that correspond to a specific search expression able to be predetermined by a user. The patient hub P here, in response to a search query Q (FIG. 2) of the application 31, returns to the application 31 a dataset list designated below as a feed 35 that contains the tweets 27 corresponding to the search query Q. The application 31 displays the received feed 35 on the device 8 GUI page of a graphical user interface GUI. A tweet 27 may be activated from this displayed feed 35, e.g., by tapping on it with a finger. In this case, the content of the tweet 27 is shown in detail in a further GUI page. The applications 32 and 33 each have a browsing function corresponding to the application 31.

Each of the applications 31-33 is configured to externalize feeds 35 on instruction from the user from the associated hub 22-24 into a local memory of the device 8, so that this feed 35 and the tweets 27 contained therein may also be displayed and/or processed by the application 31-33 without a network connection with the public cloud 13. Furthermore, each application 31-33 is configured, in response to a corresponding command of the user, to transfer externalized feeds 35 or tweets 27 to another instance of the same or of another application 31-34. For the device-internal communication of the feeds 35 or tweets 27 a local memory area, referred to as an exchange board, is set up in the memory of the device 8, to which all instances of the applications 31-34 have shared access. For exchange via the exchange board, the feeds 35 or tweets 27 to be exchanged are serialized in XML/JSON files that are stored in the local memory of the device 8 and are subsequently de-serialized. For exchange of feeds 35 and tweets 27 between different devices, the applications 31-34 may have interfaces to Twitter or to an e-mail program.

By contrast, the application 34 serves for display (e.g., viewing) of the non-alphanumeric content of an image dataset B stored in the image hub 25. Under normal circumstances, the application 34 is started from one of the applications 31-33. In particular, the application 34 is started from the application 34 assigned to the context hub 24, in that a displayed tweet 27 is activated there by the finger, by a mouse or the like (e.g., by a kind of double click). In this case, the application 34 is started, wherein the application 34 is also given the URL of the associated image dataset B extracted from the tweet 27 as an argument. The result of this is that the application 34 loads and displays the image dataset from the image hub 25 without further user interaction after it starts. Image data B may be stored in JPEG format in the image hub 25, volume data, e.g., in DICOM format. The views V (e.g., scene graphs) of volume data may be delivered from the public cloud 13 to the application 34 may be created in JPEG format. In addition, or as an alternative, image data and documents may also be stored in the image hub 25 in other formats, e.g., wbm, mp4, pdf, or dz.

Figure 3:
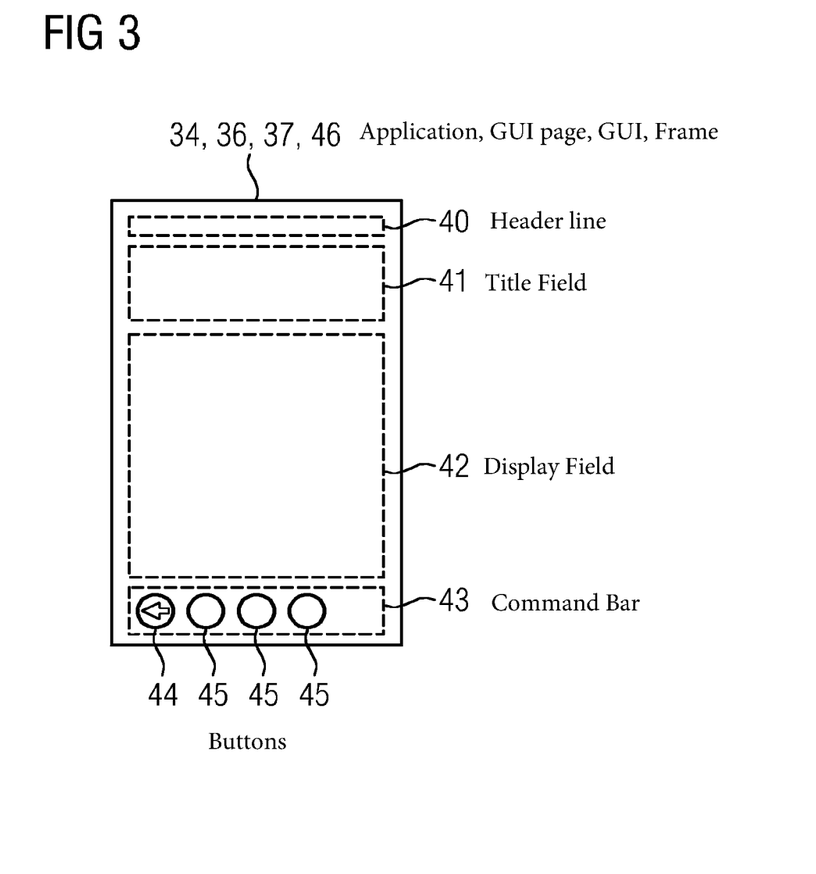
FIG. 3 depicts a schematic diagram of an example of a GUI page of a graphical user interface (GUI) intended to run on a smartphone, which is used by the viewing application assigned to the image hub for presenting the image information of an image dataset.

For this, the application 34 includes a (GUI) page 36 depicted in FIG. 3 of a graphical user interface 37.

In the exemplary embodiment in accordance with FIG. 3, the GUI page 36 has four display areas with different functions, namely a header line 40, a title field 41, a display field 42, and a command bar 43. The name of the image hub to which the application 34 is assigned is given in the header line 40. The header line 40 is thus labeled with the words "Image Hub". Furthermore, the facility 2 to which the system 1 is assigned may be named in the header line 40.

In the title field 41, the type of the displayed image dataset B is displayed, for example, as 2D viewing, 3D viewing, media viewing, document viewing, etc. In the display field 42, the visual content of the image dataset B, e.g., the image, volume, video or text document is displayed. The command bar 43 contains a button 44, in response to the actuation of which, the application 34 closes the displayed GUI page 36 and switches back to a GUI page of the browser application 31-33 last used. Further, buttons 45 serve to influence the display, for example, to enlarge (zoom-in) or reduce (zoom-out) the data content depicted in the display field 42, to start and stop and image sequence or a moving image animation, to create a key image (key), record images or sound (rec) by a camera or microphone of the device 8, etc. In addition, a button may be provided for deleting an image dataset B.

Instead, of the shared page 36 for displaying image data of all image data types, the application 34 may include different GUI pages that are each configured to display image data of a specific image data type (e.g., image, volume, video, document, etc.). The application 34 may include at least two GUI pages 36, of which one serves to display 2D image data (e.g., including photos, 2D image sequences, and videos) and the other serves to display 3D image data.

Superordinate to the GUI pages 36, the application 34 includes a frame 46. This frame 46 forms an adapter to the native runtime environment of the respective device 8, in which the application 34 runs, e.g., to the operating system, or a Web browser. The frame 46 also serves as an execution environment or container, in which a number of instances of the GUI pages 36 may be designed to run alongside one another. In the exemplary embodiment, in accordance with FIG. 3 only one of these instances is ever shown, while the others run in the background. The frame 46 may optionally make a frame of the user interface 37 available.

Figure 4:
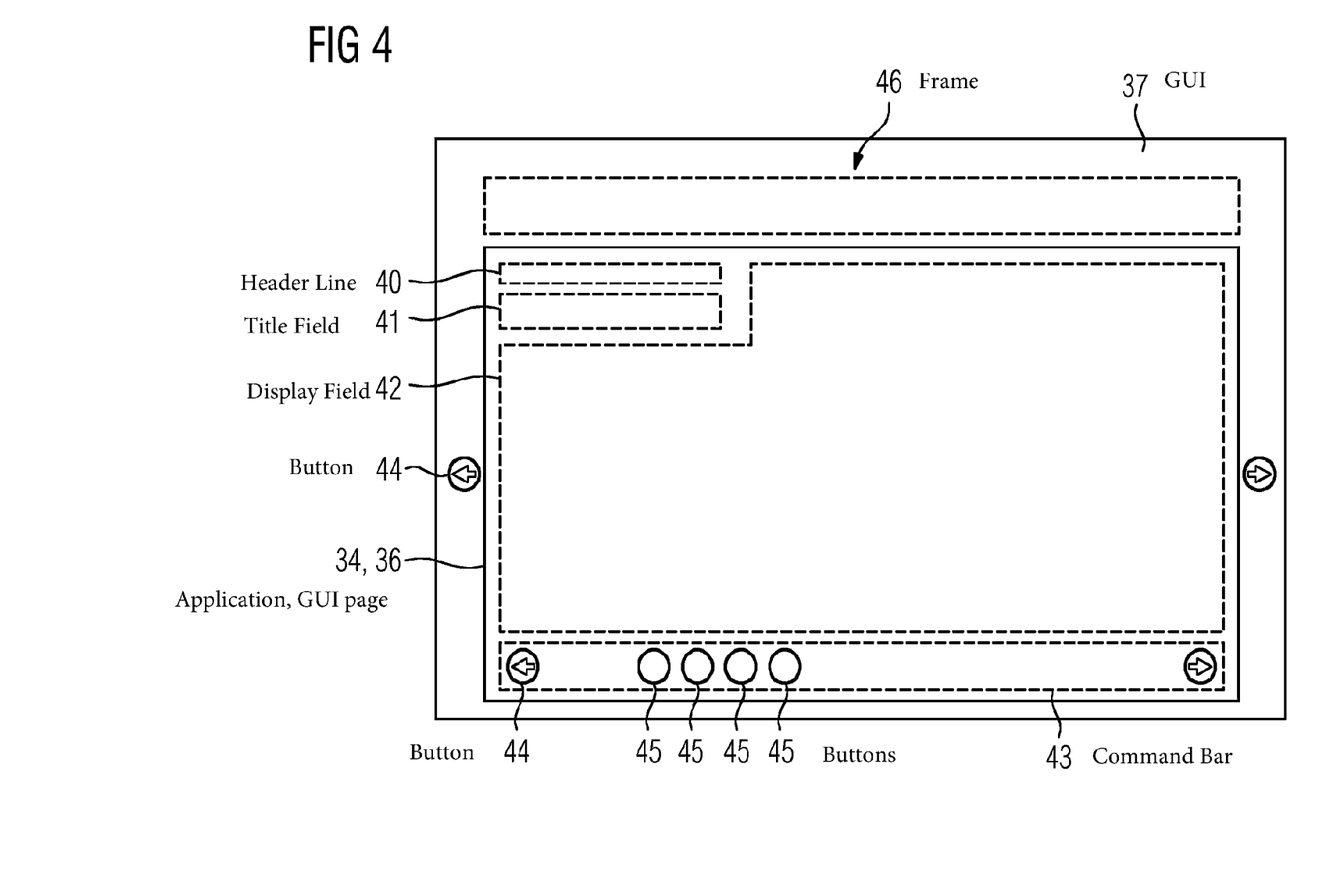
FIG. 4 depicts, in a diagram in accordance with FIG. 3, a variant of the viewing application there intended to run on a personal computer, notebook or tablet computer.

FIG. 4 depicts a version of the GUI page 36 of the application 34 optimized for display on a large-format screen, in which the display field 42 fills almost the entire screen surface of the device 8 (e.g., here in the form of the tablet computer 11).

Figure 5:
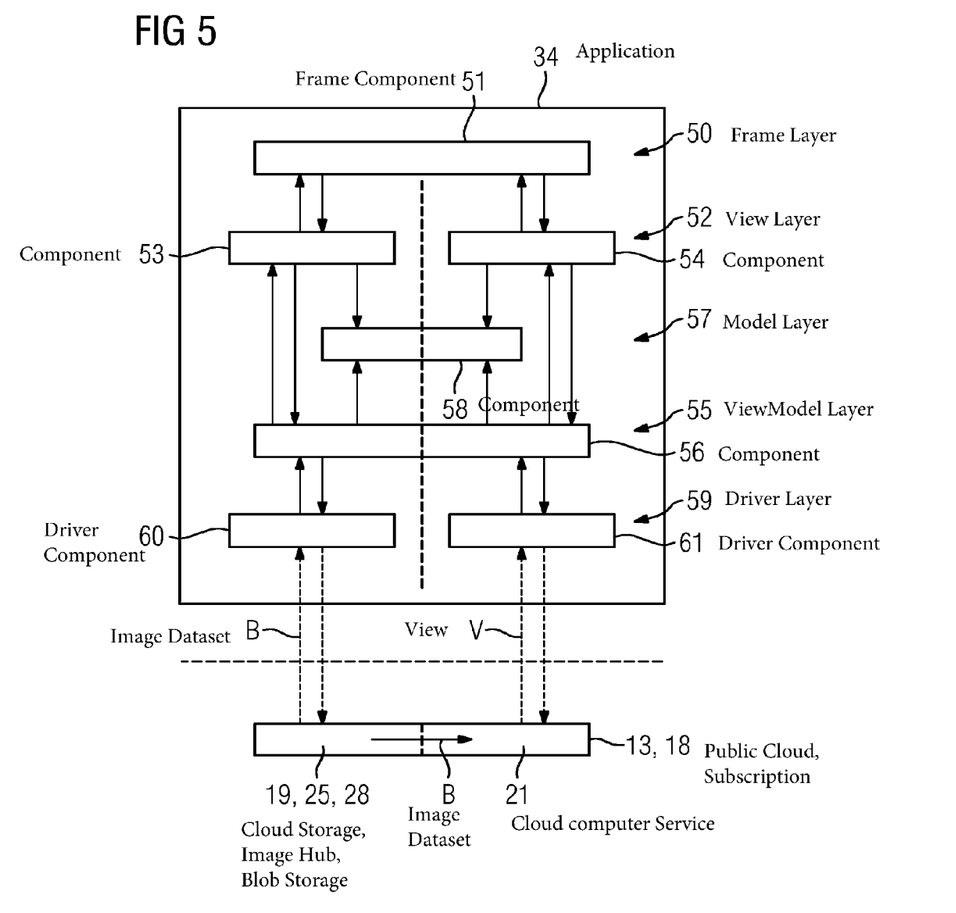
FIG. 5 depicts, in a schematic block diagram, an example of component architecture of the viewing application assigned to the image hub.

A model of the component architecture of the applications 34 is depicted schematically in FIG. 5. It may be seen from the diagram that the application 34 is formed from components that are arranged in five layers.

The highest layer of this architecture is referred to as the frame layer 50. This frame layer 50 is formed by a frame component 51, which is also referred to as a "ReadingHostAadpter" in the example in accordance with FIG. 5. The frame component 51—as explained in greater detail above—forms the frame 46 described above, e.g., a generic execution frame (container) for the GUI pages 36. The frame component 51 may regulate how control is transferred between the existing instances of the GUI pages 36 running alongside one another, e.g., how these instances are activated and deactivated for a user interaction as well as how they are displayed and removed from the screen.

The frame component 51 is specifically selected as a function of the kind of device 8 on which the application 34 is to run and is tailored to the form factor of the respective device 8 (e.g., the size and geometry of the screen) and also to the user interaction present in the device 8. For example, a version of the frame component 51 intended to be executed on the tablet computer 11 or smartphone 12 supports user interaction methods as may be used for user interaction via a touch screen (e.g., moving the GUI page 36 by manually swiping across the screen, zooming the screen information by two-finger operations, rotating the screen information by tilting the device 8, etc.). A version of the frame component 51 embodied to be executed on a personal computer 9 on the other hand provides graphical control elements in the form of buttons configured to user interaction by a mouse or touch pad. The frame component 51 may have the effect of adapting the GUI pages 36 to the respective device 8 (e.g., to the screen size) and in this context determines, for example, whether all buttons 45 or only a specific selection of buttons 45 will be displayed.

Underneath the frame layer 50 is a view layer 52. This view layer 52, in the case of the application 34, includes two components 53 and 54, which are also designated "ReadingView2D" and "ReadingView3D". The components 53 and 54 here define the view, which means the graphic design of the GUI pages 36. The component 53 ("ReadingView2D") here defines the control elements of a first variant of the GUI page 36 that is configured for display of 2D image data (including photos, key images, 2D image sequences and videos), in respect of type, appearance and arrangement. The component 54 ("ReadingView3D") on the other hand defines in a corresponding manner the control elements of a second variant of the GUI page 36 that is configured for display of 3D image data.

Furthermore, in a ViewModel layer 55 the application 34 includes a further component 56, which is designated as "ReadingViewModel". This component 56 defines for the components 53 or 54 of the View layer 52 functional characteristics and commands for the control elements of the user interface 37 defined in these components 53 or 54, e.g., functions for rotating, moving, zooming of the image information, etc. The component 56 of the ViewModel layer 95 is applied here to both components 53 and 54 of the View layer and is generic, e.g., designed independently of the type of image datasets B to be displayed to the extent that, for all types of image datasets to be displayed, namely both 2D image data and also 3D image data, it makes available a common set of functions (Play, Stop, Key, Zoom In, Zoom Out, Rec etc.) with semantics that are the same. The component 56 here equips each of these functions—as explained above—with comparable semantics for the different image data types.

In a Model layer 57, the application 34 includes a component 58, which is designated "<Tweet>ReadingModel" for example. This component 58, for each type of image data to be displayed, e.g., 2D image data for display on the screen (e.g., including the views V derived from the 3D image data) and videos, defines the variables required for holding data. The component 58 of the Model layer 57 is likewise generically designed to the extent that it may be applied to all types of image data to be displayed.

In a driver layer 59, the application 34 includes two driver components 60 and 61, which are also designated as "ReadingService2D" and "ReadingService3D". The driver components 60 and 61 act as agents for the higher-ranking layers for access to the image datasets B held in the Blob storage 28 of the image hub 25. Furthermore, the driver components 60 and 61 edit the image datasets B to be displayed, in that they derive from these image datasets B image data (e.g., frames) for direct display on the screen of the device 8 and convey it via the component 56 of the ViewModel layer 55 to the respective GUI page 36.

The driver component 60 ("ReadingService2D") serves here to load 2D image data. As may be seen from FIGS. 2 and 5, the driver component 60, in an online mode to load the image datasets B—without making use of the cloud compute services 21 or other server power—accesses the Blob storage 28 of the image hub 25 directly with an HTML request. The driver component 60 may however also be operated in an offline mode, in which it reads in the image dataset B to be displayed from the local memory of the device 8. The driver component 60 further undertakes editing of the 2D image data for display on the screen of the device 8, in that is selects or calculates a segment of the screen to be displayed, which rotates image information in response to a corresponding user request, applies specific image processing algorithms (e.g., edge sharpening or windowing) in response to a corresponding user request on the screen, etc.

The driver component 61 ("ReadingServiceAgent3D") on the other hand serves to load the image data for 3D viewing. In normal operation, the 3D image data to be displayed is therefore not loaded directly onto the device 8 by the driver component 61. Also, in the normal operation (e.g., online mode) depicted in FIG. 5, the driver component 61 does not carry out the numerically complex volume rendering itself. Instead the driver component 61 accesses the cloud compute services 21 to derive the two-dimensional views (V in the form of "rendered" image scenes) from the three-dimensional image information of the 3D image datasets, which load the image datasets B autonomously from the cloud 13 from the Blob storage 28 of the image hub 25 and only return the completed "rendered" views V to the driver component 61.

The driver component 61 may also be operated in an offline mode in an optional embodiment, in which it loads the 3D image datasets B to be displayed, (e.g., from a local memory of the device 8), and creates the two-dimensional views V locally.

Both driver components 60 and 61 process request by the component 56 of the ViewModel layer 55 asynchronously and in parallel. In the spirit of the most efficient data flow possible, the driver components 60 and 61 are designed so that they do not respond directly to queries, but only respond with the result, e.g., with the frame created in accordance with the query. Likewise, in the spirit of data processing and transmission that is as efficient as possible, the driver component 61 is additionally designed so that, for each view V to be created, in accordance with a single-instruction-per-frame principle, it only issues a single message (per HTTP request R) to the cloud compute services 21. To this end, the driver component accesses a broad, singular application program interface (API), which only includes a single method bearing all necessary parameters.

The functionality for displaying the 3D image data is an optional function of the application 34 that may be connected reversibly at the request of a user (on-demand) or within the framework of a license option. Accordingly, the application 34 may also be operated without the component 54 and the driver component 61. In the case of a corresponding user request, the component 51 and the driver component 61 are reloaded or activated here.

The application 34 may be permanently installed on the device 8 or may be provided for download in the App Store 20. In the former case, the application 34 is called by specifying as an argument the URL 29 of an image dataset B to be displayed. In the latter case, the application is designed such that, in the download request, in addition to the URL of the application 34, the URL of the image dataset B to be displayed may be specified as the argument.

In both cases, the URL 29 specified as the argument is given by the frame component 51 to the component 56 of the ViewModel layer 55. Here, the type of image dataset B to be displayed is determined on the basis of the URL 29. Depending on the type of image data established, the component 56 selects the appropriate component 53, 54 of the View layer 52, and the appropriate driver component 60, 61 of the driver layer 59. For 2D image data (with the exception of video streams, which are controlled directly by the component 56), the component 56 thus selects the driver component 60, while it selects the driver component 61 for 3D image data. Furthermore, the component 56 (e.g., by corresponding activation of the driver components 60, 61) causes the loading of the image data to be displayed. Thus, the image dataset B, or in the case of 3D image data, possibly the first view V derived therefrom, is loaded and displayed by the application 34 after the start of the application 34 without further user interaction.

In order to download the application 34, the frame component 51 suitable for the device 8 may be first downloaded from the App Store 20. The frame component 51 also serves as application configurator here, in that it reloads the necessary components of the subordinate layers on the basis of an application template held as an XML file in the App Store 20.

With the function "Key" (e.g., for creating a key image K) and "Rec" (e.g., for recording images and/or sound by the camera or microphone of the device 8), the application 34 makes it possible to create new image datasets B. These will be loaded by the component 56 by an HTML POST command directly (without intermediate cloud compute services 21 or other server power) into the image hub 25.

The invention is made clear by the exemplary embodiments described above, but equally is not restricted to the embodiments. Instead further forms of embodiment of the invention may be derived from the present description and the claims. In particular, the individual features of the invention described on the basis of the exemplary embodiments may also be combined in another way, without departing from the invention.

Given in the subsequent annexes are examples for a concrete implementation of the View layer 52 ("Reading ViewModel2D3D.html") and the component 56 ("ReadingViewModel.js) of the View model—layer 55—grouped here into one component.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

---

Annex 1: Example implementation of the View layer 52 - „ReadingView2D3D.html"

```
<!DOCTYPE html>
<html>
<head>
    <title>Syngo 2D/3D Reading-Device-App</title>
    <meta name="demopage" content="1" /><meta http-equiv="X-UA-Compatible" content="IE=edge" />
    <script src="js/jquery-1.7.2.js"></script>
    <link rel="stylesheet" href="css/ReadingView2D3D.css" />
    <script src="js/uInt8Array_getter_setter.js"></script>
    <script src="js/StringFormatter.js"></script>
    <script src="js/Point.js"></script>
    <script src="js/InstanceInfo.js"></script>
    <script src="js/ReadingServiceAgent3D.js"></script>
    <script src="js/arrayBufferToDataUri_Common.js"></script>
    <script src="js/uInt8Array_IE9.js"></script>
    <script src="js/ReadingViewModel.js"></script>
    <script src="js/ReadingServiceAgent2D.js"></script>
    <script type="text/javascript" src="js/FeatureDetectCanvas.js"></script>
    <script src="js/ReadingService2D.js"></script>
</head>
<body>
    <div id="workspace">
        <div id="NavigationAppBar">
            <input type="image" onclick="GUI_ViewDetail_Click( )" src="images/ApplicationBar.Check.png" id="qualityButton">
            <input type="image" onclick="GUI_SwitchAppBar_Click( )" src="images/ApplicationBar.Refresh.png" id="switchAppBarButton">
        </div>
        <div id="ViewingAppBar">
            <input type="image" onclick="GUI_ApplicationBarIconButton_ROTATE_Click( )" src="images/ApplicationBar.Rotate.png" id="rotateButton">
            <input type="image" onclick="GUI_ApplicationBarIconButton_WINDOWING_Click( )" src="images/ApplicationBar.Windowing.png" id="windowingButton">
            <input type="image" onclick="GUI_ApplicationBarIconButton_START_Click( )" src="images/ApplicationBar.Start.png" id="startButton">
            <input type="image" onclick="GUI_ApplicationBarIconButton_2D_Click( )"
```

Annex 1: Example implementation of the View layer 52 - „ReadingView2D3D.html"

```
src="images/ApplicationBar.2D.png" id="zweiDButton">
    <input type="image"
onclick="GUI_ApplicationBarIconButton_SaveKeyIma_Click( )"
src="images/ApplicationBar.Save.png" id="saveKeyImaButton1">
    <input type="image" onclick="GUI_ApplicationBarIconButton_Import_Click( )"
src="images/ApplicationBar.Download.png" id="importButton1">
    <input type="image" onclick="GUI_ApplicationBarIconButton_Export_Click( )"
src="images/ApplicationBar.Upload.png" id="exportButton1">
  </div>
  <div id="DrawingAppBar">
    <input type="image" onclick="setColor(0,0,0)" src="images/black1.png"
id="blackButton">
    <input type="image" onclick="setColor(0xff,0,0)" src="images/red.png"
id="redButton">
    <input type="image" onclick="setColor(0,0xff,0)" src="images/green.png"
id="greenButton">
    <input type="image" onclick="setColor(0,0,0xff)" src="images/blue.png"
id="blueButton">
    <input type="image" onclick="setPen(10)" src="images/thick3.png"
id="thickButton">
    <input type="image" onclick="setPen(5)" src="images/middle3.png"
id="mediumButton">
    <input type="image" onclick="setPen(1)" src="images/thin3.png"
id="thinButton">
    <input type="image" onclick="clearCanvas( )"
src="images/ApplicationBar.Cancel.png" id="clearButton">
    <input type="image"
onclick="GUI_ApplicationBarIconButton_SaveKeyIma_Click( )"
src="images/ApplicationBar.Save.png" id="saveKeyImaButton2">
    <input type="image" onclick="GUI_ApplicationBarIconButton_Import_Click( )"
src="images/ApplicationBar.Download.png" id="importButton2">
    <input type="image" onclick="GUI_ApplicationBarIconButton_Export_Click( )"
src="images/ApplicationBar.Upload.png" id="exportButton2">
  </div>
  <div id="PerfCounter" > <p id="fps" > </p> </div>
  <div id="Image1" > <img id="msi2" src=""/> </div>
  <div id="Canvas1" > <canvas id="msi1" ></canvas> </div>
  <div id="title"> </div>
  <div id="container" style="text-align: center;"> </div>
  <div id="hotspots"> </div>
 </div>
</body>
</html>
```

The invention claimed is:

1. A system for management and processing of data of a medical facility, the system comprising:
    at least one viewing application for execution by a processor and stored in memory on a user device, wherein the viewing application is configured for displaying medical image datasets held in cloud storage of a public cloud such that each of the medical image datasets is accessible via an associated Uniform Resource Locator (URL) when a corresponding cloud subscription is available, wherein the viewing application is further configured to be downloaded via an associated URL from the cloud storage of the public cloud when the corresponding cloud subscription is available, wherein the URL of the image dataset to be displayed is configured to be specified as an argument, wherein the viewing application comprises:
    a View layer comprising at least one component that defines graphical content of a graphical user interface (GUI) page for display of two-dimensional (2D) image data or three-dimensional (3D) image data;
    a ViewModel layer comprising one component, which, for a component or each component of the at least one component of the View layer, defines functions for the control elements of the GUI page for display and processing of the image data;
    a Model layer comprising one component that defines variables for the image data to be displayed; and
    a driver layer comprising:
        a component configured to load 2D datasets and edit the 2D datasets for display on a screen; and
        a further component that is loadable or activatable as an option, the further component configured to load 3D image datasets or two-dimensional views derived therefrom and edit the 3D image datasets or two-dimensional views for display on a screen,
    wherein the component of the ViewModel layer defines a common set of functions for the display and processing of the 2D image data and the 3D image data.

2. The system of claim 1, further comprising:
    a Frame layer superordinate to the View layer, the Frame Layer comprising a component that makes available a generic execution frame for the component or for each component of the View layer.

3. The system of claim 2, wherein the component and the further component of the driver layer are each configured to process requests from components of superordinate layers asynchronously and in parallel, and
    wherein the component and/or the further component of the driver layer only respond by returning the image data loaded and/or edited because of the request.

4. The system of claim 3, wherein the component of the driver layer for loading the 2D image data is configured to load image datasets from a predetermined data memory directly without a server acting as an agent.

5. The system of claim 4, wherein the further component of the driver layer for loading the 3D image data or the two-dimensional views derived therefrom is configured to access cloud compute services in an online operating mode to create the two-dimensional views from the 3D image dataset to be displayed.

6. The system of claim 1, wherein the component and the further component of the driver layer are each configured to process requests from components of superordinate layers asynchronously and in parallel, and
wherein the component and/or the further component of the driver layer only respond by returning the image data loaded and/or edited because of the request.

7. The system of claim 1, wherein the component of the driver layer for loading the 2D image data is configured to load image datasets from a predetermined data memory directly without a server acting as an agent.

8. The system of claim 7, wherein the component of the driver layer for loading the 2D image data is configured to load the image data by direct access to the cloud storage of the public cloud.

9. The system of claim 1, wherein the further component of the driver layer for loading the 3D image data or the two-dimensional views derived therefrom is configured to access cloud compute services in an online operating mode to create the two-dimensional views from the 3D image dataset to be displayed.

10. The system of claim 9, wherein the further component of the driver layer for loading the 3D image data or the two-dimensional views derived therefrom is additionally configured, in an offline mode, to load the data to be displayed directly from a data memory without making use of an intermediate server and to derive on the user device the two-dimensional views of the three-dimensional image information for display on a screen of the user device.

11. The system of claim 1, wherein the viewing application for displaying an image dataset is configured to be called by specifying the URL of the image dataset as an argument.

* * * * *